United States Patent
van den Brink (10) Patent No.: US 10,317,348 B2
(45) Date of Patent: Jun. 11, 2019

(54) METHOD OF AND DEVICE FOR RECEIVING AND CHECKING INDIVIDUALIZED DOSES OF MEDICINES

(71) Applicant: Global Factories Total Engineering and Manufacturing B.V., 's-Gravenhage (NL)

(72) Inventor: Richard Rudolf Theodoor van den Brink, 's-Gravenhage (NL)

(73) Assignee: GLOBAL FACTORIES TOTAL ENGINEERING AND MANUFACTURING B.V., 'S-Gravenhage (NL)

(*) Notice: Subject to any disclaimer, the term of this patent is extended or adjusted under 35 U.S.C. 154(b) by 0 days.

(21) Appl. No.: 15/120,420

(22) PCT Filed: Feb. 23, 2015

(86) PCT No.: PCT/NL2015/050113
§ 371 (c)(1),
(2) Date: Aug. 19, 2016

(87) PCT Pub. No.: WO2015/126254
PCT Pub. Date: Aug. 27, 2015

(65) Prior Publication Data
US 2017/0016836 A1     Jan. 19, 2017

(30) Foreign Application Priority Data
Feb. 21, 2014  (NL) ...................................... 2012310

(51) Int. Cl.
*G07F 17/00*  (2006.01)
*G01N 21/95*  (2006.01)
(Continued)

(52) U.S. Cl.
CPC ........ *G01N 21/9508* (2013.01); *A61J 7/0069* (2013.01); *A61J 7/0084* (2013.01);
(Continued)

(58) Field of Classification Search
CPC .................................................. G07F 17/0092
(Continued)

(56) References Cited

U.S. PATENT DOCUMENTS 7,641,073 B2 * 1/2010 Kim ........................ B65B 5/103
                                                                221/171
8,914,148 B2 * 12/2014 Wagner ................. G06F 19/327
                                                                700/236
(Continued)

FOREIGN PATENT DOCUMENTS

CN        101802830 A       8/2010
EP           2082718         7/2009
(Continued)

OTHER PUBLICATIONS

International Search Report from App No. PCT/NL2015/050113 dated Apr. 22, 2015.
(Continued)

*Primary Examiner* — Timothy R Waggoner
(74) *Attorney, Agent, or Firm* — Adsero IP (57) ABSTRACT

A method of receiving and checking individualized compound doses of medicines the steps of receiving a plurality of dispensed medicines that form an individualized compound dose of medicines, assessing the composition of the individualized compound dose of medicines trough automated recognition of the received medicines, checking the assessed composition of the received individualized compound dose of medicines against a record for the composition of that individualized compound dose of medicines, and if the outcome of the check is positive, discharging the (Continued)

received individualized compound dose of medicines to be packaged in a dose compartment of a multi dose compartment package, and if the outcome of the check is negative, discharging the received individualized compound dose of medicines other than to be packaged in a dose compartment of the multi dose compartment package. The disclosure also includes a device for receiving and checking individualized compound doses of medicines.

25 Claims, 6 Drawing Sheets

(51) Int. Cl.
    *A61J 7/00*     (2006.01)
    *G01N 21/65*     (2006.01)

(52) U.S. Cl.
    CPC ......... *G01N 21/65* (2013.01); *G07F 17/0092* (2013.01); *G01N 2201/12* (2013.01)

(58) Field of Classification Search
    USPC .................................................. 700/231–244
    See application file for complete search history.

(56) References Cited

U.S. PATENT DOCUMENTS

| | | | |
|---|---|---|---|
| 9,428,288 B2* | 8/2016 | Shigeyama | B65B 5/103 |
| 2002/0108892 A1 | 8/2002 | Goetz | |
| 2008/0059228 A1* | 3/2008 | Bossi | G06F 19/3418 705/2 |
| 2009/0133362 A1* | 5/2009 | Bentele | B65B 5/103 53/54 |
| 2009/0321472 A1* | 12/2009 | Knoth | B65B 5/103 221/124 |
| 2012/0290129 A1 | 11/2012 | Luciano, Jr. | |
| 2013/0169798 A1* | 7/2013 | Pellerin | G06F 19/3462 348/135 |
| 2013/0284755 A1* | 10/2013 | Yuyama | A61J 7/02 221/13 |
| 2014/0236349 A1* | 8/2014 | Bae | G06F 19/3462 700/236 |
| 2014/0318078 A1* | 10/2014 | Kondo | B65B 57/10 53/54 |
| 2017/0057682 A1* | 3/2017 | Chudy | B65B 11/52 |

FOREIGN PATENT DOCUMENTS

| | | |
|---|---|---|
| JP | 2000-325430 | 11/2000 |
| WO | WO 2005/017814 | 2/2005 |
| WO | WO 2013/105198 | 7/2013 |

OTHER PUBLICATIONS

Office Action from EP 15710945.5 dated Oct. 20, 2017.
Office Action from JP App No. 2016-553590 dated Dec. 4, 2018 (with English translation).
Office Action from CN App No. 201580020816.3 dated Aug. 1, 2018, English translation only.

* cited by examiner

METHOD OF AND DEVICE FOR RECEIVING AND CHECKING INDIVIDUALIZED DOSES OF MEDICINES

RELATED APPLICATIONS

This application is a 35 U.S.C. § 371 national phase application of PCT/NL2015/050113 (WO 2015/126254), filed on Feb. 23, 2015, entitled "Method of and Device for Receiving and Checking Individualized Doses of Medicines", which application claims priority to Netherlands Application No. 2012310, filed Feb. 21, 2014, each of which is incorporated herein by reference in its entirety.

The invention relates to individualized compound doses of medicines, in particular pills.

For medicine users that use a plurality of different medicines, it is often difficult to ensure that at each intake moment, a prescribed combination of medicines is taken. In order to facilitate taking the prescribed combination at each intake moment, it has been proposed to prepare individualized compound doses of medicines, and to prepackage these doses according to subsequent intake moments for a particular patient.

In practice, for each of a series of subsequent intake moments, pills are collected from selected cassettes of a dispensing machine to form an individualized compound dose of medicine in accordance with a patient prescription record, and the doses are individually packaged in a string of sealed packages. In order to ensure the correctness of the compound doses, the composition of each sealed package in the string is assessed and checked in an automated process, e.g. in accordance to WO2005/017814.

Although highly effective, this process still has disadvantages. For example, in case the check reveals a dose has not been composed properly, e.g. because a pill failed to leave a cassette or got caught in a dispenser chute, a package in the string is rejected. In case a package in the string is rejected, the string either needs to be discarded or the composition of the dose in the rejected package in the string needs to be amended and rechecked manually. Also, in case a dose cannot be composed as prescribed, e.g. because the store of a medicine in a cassette has run out, the dispensing process is stopped.

The invention aims to alleviate the above disadvantages. Thereto the invention provides for a method of receiving and checking individualized compound doses of medicines, comprising repetition of the steps of:

receiving a plurality of dispensed medicines that form an individualized compound dose of medicines, assessing the composition of the individualized compound dose of medicines trough automated analysis of the received medicines, checking the assessed composition of the received individualized compound dose of medicines against a record for the composition of that individualized compound dose of medicines, and if the outcome of the check is positive, discharging the received individualized compound dose of medicines to be packaged in a dose compartment of a multi dose compartment package, and if the outcome of the check is negative, discharging the received individualized compound dose of medicines other than to be packaged in a dose compartment of the multi dose compartment package.

By assessing and checking the composition of the individualized doses before packaging, it may be achieved that only doses with a positive check on their composition are packaged. This way, it may be prevented that a string of packages is rejected because a packaged dose in the string is of the wrong composition. It is noted that it is also possible that the step of discharging the received individualized compound dose of medicines to be packaged in a dose compartment of a multi dose compartment package when the outcome of the check is positive, may comprise an intermediate step. That is that if the outcome of the check is positive, discharging the received individualized compound dose of medicines to be packaged first to a tray, e.g. a buffer tray prior to discharging it to a dose compartment of the multi dose compartment package. The tray may comprise multiple compartments for sorting medicines. In particular, the bottom of the tray may, e.g. open such that the multi dose compartment package may then received the individualized compound dose of medicines from the tray. Other ways of discharging medicines from the tray to the multi dose compartment package may also be possible. For example, an open surface of the multi dose compartment package is put onto an open surface of the tray, and subsequently the tray and/or the multi dose compartment package may be flipped.

The step of automated analysis may include optical recognition, and in particular may include storing photographic images of the actual individual compounded doses. The method steps are in principle consecutive, but may at least partially overlap for a given individualized compound dose. The method is for sequentially composing individualized compound doses of medicines, but the steps for consecutive individualized compound doses of medicines may take place simultaneously, i.e. processed in parallel, but mutually staggered in step.

A previously received individualized compound dose of medicines may be assessed and/or checked, while a following individualized compound dose of medicines is being received. This way, the output may be increased. In particular, receiving a following dose in separate reception area while a previous dose is assessed allows for buffering. This way, a dose that is being received may come to rest before it is subject to assessment. This is particularly advantageous in case the medicines include pills that are relatively hard, as they tend to bounce. It should be noted that a following individualized compound dose of medicines may be a later received dose, but need not be a next dose, as there may be buffering of several doses.

After reception in a reception area, a received individualized compound dose of medicines may be moved to a separate assessment area. Such separation may prevent that the receiving process disturbs the assessment process. The reception and assessment areas may be spatially separate, but preferably are also physically separated.

A received and checked individualized compound dose of medicines may be discharged, while a subsequently received individualized compound dose of medicines is being assessed and/or checked. This further increases efficiency.

After checking in an assessment area, a received and assessed/checked individualized compound dose of medicines may be moved to a separate discharging area for discharging. This way, it may be achieved that any time needed for the discharging step does not increase the time needed for assessment and checking. The assessing and discharging areas may be spatially separated, but preferably are also physically separated.

After discharge of a received and checked individualized compound dose of medicines, a discharging area may be inspected for any remaining medicines. This may e.g. be done by automated optical inspection, and an optical image, specifically a digital photo, of the discharging area after discharge may be stored in a record for the individualized compound dose of medicines, e.g. along with an optical image, specifically a digital photo, of an assessment area containing the dose.

A multi dose compartment package may be indexed with a dose compartment to receive a discharged individualized compound dose of medicines. The multi dose compartment package may e.g. be indexed with a dose compartment thereof to be positioned to have its position correspond with an exit of a chute connected to the discharging area. For each received individualized compound dose of medicines, the multi dose compartment package may be virtually and/or physically indexed to another free dose compartment.

If the outcome of the check is negative, that dose compartment may then be skipped and may remain open to receive an individualized compound dose of medicines. If the outcome of a check is negative, a plurality of medicines to form an individualized compound dose of medicines according to that record may be received a second time, and the multi dose compartment package may be indexed to the skipped dose compartment to package the individualized compound dose of medicines. This indexation may e.g. take place upon discharge, in case the check on the composition of the dose that is received a second time, is positive. This way, in case a dose is found to have an incorrect composition, the packaging process may continue with packaging a of buffered dose that is found to have a correct composition in a compartment assigned thereto, and a gap in a string of compartments packaged with doses may thus be temporarily formed at the compartment that corresponds to the incorrectly composed dose, which may be filled later when a correctly composed dose for that package is discharged to be packaged.

The dose compartments in the multi dose compartment package may each be dedicated for the individualized compound doses of medicines according to a specific record. The dose compartments may each be provided with an unique physical identifier for the individualized compound dose of medicines in or for that compartment, e.g. a number. The identifier for the dose compartment may be provided previously, and may be coupled to the record, or may be generated for that record and provided to the dose compartment after or upon discharge of the dose.

The dose compartments in the multi dose compartment package may conveniently be closed only after all the individualized compound doses of medicines for that package have been packaged.

The composition of individualized compound doses of medicines contained in dose compartments of the package may be assessed via automated recognition of the medicines contained in compartments, and may be checked against a record for the composition of the individualized compound dose of medicines for that compartment. The automated recognition preferably includes optical recognition. The assessment may include capturing an optical image, in particular taking a digital photo, and analyzing the image to extract pill identifying characteristics, including e.g. size, shape, color, texture and markings. The captured image may be compared to images stored in a database or library.

The repeated steps may include a first step of automatically dispensing medicines from selected ones of a plurality of storages of mutually different medicines in accordance with a record for an individualized compound dose of medicines. The repeated steps may further include an alternative first step of manually dispensing mutually different medicines in accordance with a record for an individualized compound dose of medicines.

The invention further provides for a device arranged to receive and check individualized compound doses of medicines arranged to perform the steps as described above, individually or in combination.

Specifically, the invention provides for a device arranged to read, check and, if the check is positive, thereafter discharge to be packaged individualized compound doses of medicines, in particular according to the method steps of any of claims 1-15.

A device for receiving and checking individualized compound doses of medicines may comprise:
- a receiving area for receiving a plurality of dispensed medicines that form an individualized compound dose of medicines,
- an assessment area with automated recognition apparatus for assessing the composition of the individualized compound dose of medicines trough automated recognition of the received medicines,
- a computer that, in particular prior to discharging to be packaged and/or prior to packaging, checks the assessed composition of the received individualized compound dose of medicines against a record for the composition of that individualized compound dose of medicines, and
- a discharge that, if the outcome of the check is positive, discharges the received individualized compound dose of medicines to be packaged in a dose compartment of a multi dose compartment package, and if the outcome of the check is negative, discharges the received individualized compound dose of medicines other than to be packaged in a dose compartment of the multi dose compartment package.

By embodying the receiving area as a dose buffer that is physically separate from the assessment area, it may be achieved that the medicines comprising the dose may be collected and come to rest while a previously collected dose is being collected.

The device may include a packaging facility arranged to receive checked individualized compound doses of medicines to be packaged from the discharge. Through this integrated packaging, the reliability of the process may be enhanced further.

The device may comprise a number of transport receptacles that are arranged to receive a dose from the dose buffer, and to confine it in the receptacle during transport. This way, a dose of medicines may be transported along various processing areas, e.g. an assessment area and a discharge area without risk of losing medicines from the dose. Such a transport receptacle may receive collected doses of medicines via a drop bottom in the dose buffer. The transport receptacle(s) may be ring shaped, in particular with an open top and bottom, and may be arranged to slide over a hard bottom, e.g. a steel and/or glass plate.

The transport receptacles may be arranged to transport the dose from an assessment area to a discharge area. The assessment area may e.g. be provided with a top and/or bottom camera to capture optical images of the dose, lights to enhance the image, backlights to provide lighting, a semitransparent mirror to allow either reflection of the image enhancing light or backlight, and/or a shaker to bring medicines in a dose out of stacked or overlapping arrangement.

Transport receptacles may be arranged to be indexable, e.g. between an assessment area and a discharge area. The discharge area may include a chute connected to an aperture in the hard bottom plate.

The device may further include a table arranged to carry a multi dose compartment package, which table is positionable in its plane to align dose compartments of the multi dose compartment package with a dispensing zone corresponding to the discharge area. It is noted that the table may carry an intermediate tray that may have multi compartments to receive medicines from the discharge. The intermediate tray may then be aligned with a multi dose compartment package such that medicines may be discharged from the intermediate tray to the multi dose compartment package.

The device may further include a disposal, alignable with the discharge area, e.g. a bin, or a tray with separate compartments for holding incorrectly compounded doses. Using such separate compartments facilitates recycling the individual medicines in the incorrectly compounded doses, e.g. for reclispensing. Alternatively or in addition, the composition of incorrectly compounded doses may be manually amended, and the corrected dose may be fed back to a receiving area or checking area of the machine. These may also be provided on the table.

The device may further including a reader unit for reading a code on a multi dose compartment package carried on the table, and may include a writer unit to write codes on individual packages of the multi package.

It should be noted, that the method steps and technical features described above may each on its own be embodied in a method or device for receiving and checking individualized compound doses of medicines, i.e. isolated from the context in which it is described, separate from other steps or features, or in combination with only a number of the other steps or features described in the context in which it is disclosed. Each of these steps or features may further be combined with any other step or feature disclosed, in any combination.

The invention will be further elucidated on the basis of a non-limitative exemplary embodiment which is represented in a drawing. In the drawing:

It is noted that the figures are merely schematic representations of a preferred embodiment of the invention. In the figures, identical or corresponding parts are represented with the same reference numerals.

Figure 1:
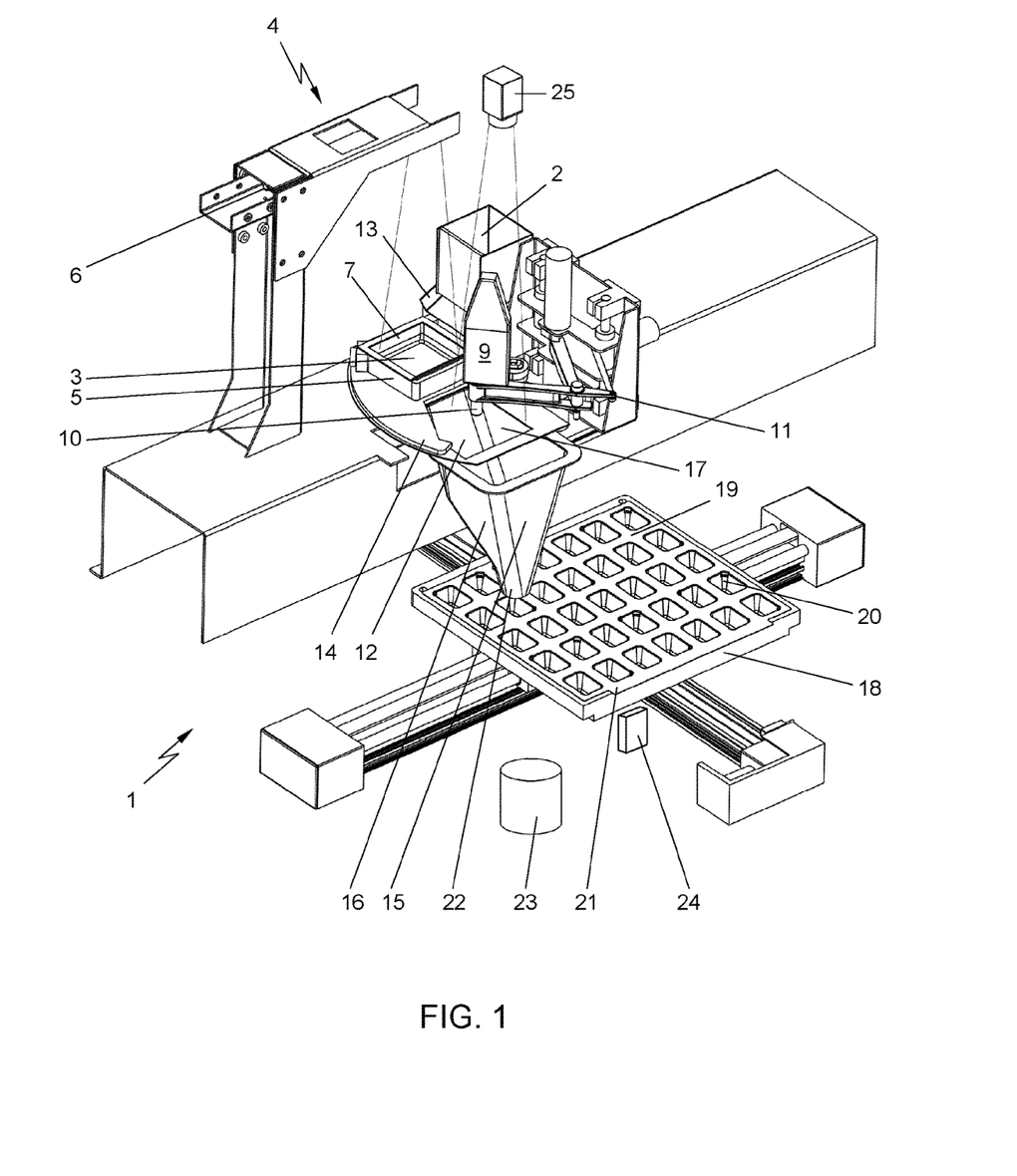
FIG. 1 shows a schematic front perspective view of a device for receiving and checking individualized compound doses of medicines.
Figure 2:
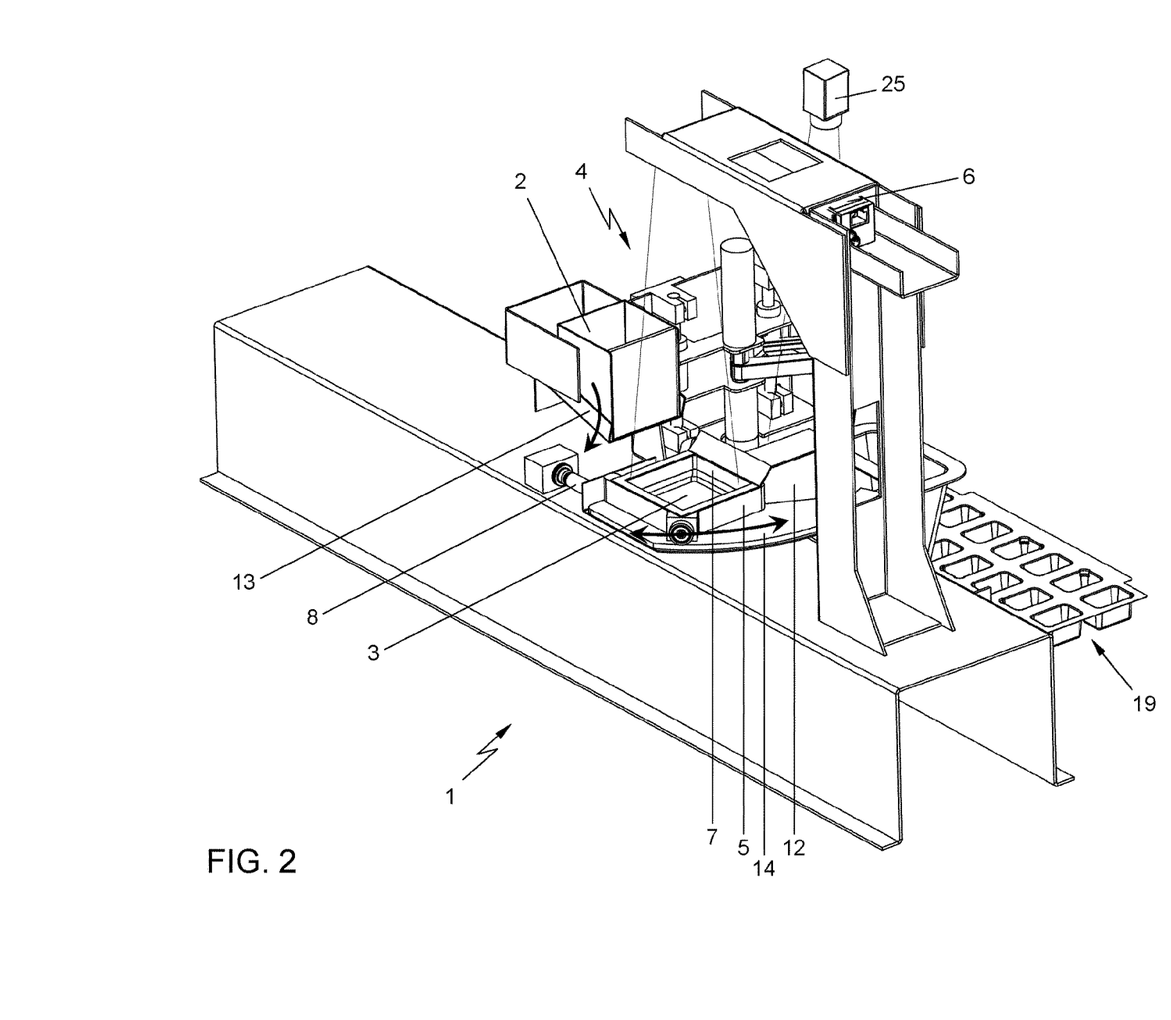
FIG. 2 shows a schematic rear perspective view of the device of FIG. 1.

FIGS. 1 and 2 show a device for receiving and checking individualized compound doses of medicines.

DESCRIPTION OF THE DEVICE

The device 1 comprises a receiving area for receiving a plurality of dispensed medicines that form an individualized compound dose of medicines. The receiving area is embodied as a dose buffer 2 in which the medicines comprising the dose may be collected and come to rest.

The device 1 may advantageously be provided with a counting sluice in the path along which the medicines must pass on their way to a destination in the medicine dispensing machine, in particular the receiving area and/or the checking area. In the sluice, the number of medicines travelling through the sluice may be counted and may then be compared to the number of medicines in the individualized compound dose of medicines that is dispensed. This way, it is known when the complete dose has passed. When the sluice is placed upstream in proximity to the receiving or checking area, it may be assumed that the complete dose of medicines has arrived at the destination, e.g. a checking or receiving area, shortly after they have passed through the sluice, so that the dose is ready to be transferred from the receiving area to the checking area. This way, the checking process can begin without having to calculate with a standard travel time of the dispensed medicines, or without waiting until the medicines have come to rest to be counted. In operation, this may save significant amounts of time. The counting sluice may include any type of sensor or sensor array having a quick response, and may e.g. preferably be embodied as an optical sluice, e.g. a light sluice that includes a fotocell array, a scanner sluice that includes a laser scanner, or a camera sluice that includes a set of cameras arranged at an angle to each other. It shall be clear that such a counting sluice may also be used advantageously in any type of device for dispensing and/or checking of compound doses of medicines.

The device 1 further includes an assessment area with automated recognition apparatus 4 for assessing the composition of the individualized compound dose of medicines trough automated recognition of the received medicines. The assessment area is identified as a dose check position 3 where a receptacle is 5 is situated. The dose buffer 2 is physically separate from the assessment area.

The automated recognition apparatus 4 includes a top digital camera 6, and a bottom digital camera (not shown) to take photos of the dose at the checking position. The automated recognition apparatus 4 in the example further includes auxiliary equipment, such lights 7 to enhance lighting of the pills at the dose check position 3. The device 1 also comprises a semitransparent mirror (not shown) to allow either reflection or passing through of image enhancing light emitted from bottom lights (not shown) so as to allow for an image to be taken against the light to get a clear image of the contours of the pills. Further the device comprises a shaker 8 to bring medicines contained in a dose out of stacked or overlapping arrangement.

Advantageously, the shaker may be arranged as an exciter that excites the assessment area in a limited number of excitations, preferably a set of 5 excitations or less, more preferably 3 or less of most preferably only a single or double excitation. By applying only a few taps, nudges or jogs as excitations, a significant amount of time can be saved in the checking process, as the shaker can deliver the set of excitations in a fraction of a second, while the amount of energy transferred onto the pills can be kept small so that the medicines quickly return to a resting position in which they can be assessed. It shall be clear that such an exciter may also be used advantageously in any type of device for dispensing and/or checking of compound doses of medicines. Further equipment part of the recognition apparatus 4 in this example includes a spectroscopy device 9 based on Raman spectroscopic analysis. The spectroscopy device 9 includes a spectroscopy head 10 with a radiation emitting fibre and a positioning arm 11 with which the spectroscopy head 10 may be positioned at a particular pill. The spectroscopy head may be positioned at a predetermined distance from the top or bottom surface of the pill to be assessed. Preferably, the positioning arm 11 positions the spectroscopy head 10 at the center of a pill to be assessed, at a predetermined height above or below the center. The predetermined distance of the spectroscopy head 10 may be a fixed height relative to the surface that the pill lies on, i.e. the glass plate 14, or may be a fixed height relative to the top surface of the pill, e.g. determined with a distance probe. Conveniently, the spectroscopy head 10 may be positioned near or against the bottom of the plate 14 measuring upward, so that the predetermined distance may be the thickness of the plate that the pill lies on. This way it is relatively simple to obtain accurate measurements with high reproducibility, while reference measurements are also relatively simple to collect in a test device which includes the same configuration of the head and plate onto which the pills are put. The center of the pill or other positions where the spectroscopic measurement is to be taken, may be determined from the image obtained via the camera. The spectroscopy head 10 will then irradiate a surface of a particular pill at a predetermined height with a laser beam. A reflected spectrum measurement is determined by inter alia the density of the pill. In case the pill is not homogeneous, several spectroscopic measurements may be taken at several predetermined positions around the pill, e.g. in a 1-2 mm diameter circle.

The reflected spectrum measurement is determined by the density of a particular pill, the height/position of the spectroscopy head 10 with respect to a point on the top surface of the pill and the power of the laser beam. Preferably, power of the laser is minimized to ensure a minimum irradiation time of the pill and to prevent degradation of the pill due to the laser beam.

The spectroscopic measurement may then be compared to stored spectroscopic measurements taken at a same position and at the same height for reference pills. Thus, a specific pill can be identified in a simple way. The Raman spectroscopic analysis can also being used to eliminate doubts in case the visual information collected is not yet enough to identify a specific pill, or e.g. to verify that a pill is genuine and not a fake. It should be noted that such Raman spectroscopic analysis of medicines in assessment of the composition of an individualized compound dose of medicines is an invention in itself, and is also applicable in any type of prior art device for assessment, including post packaged assessment.

In addition, the device includes a computer (not shown) that checks the assessed composition of the received individualized compound dose of medicines against a record for the composition of that individualized compound dose of medicines. This shall be discussed more in detail further on, and is preferably carried out prior to discharging to be packaged and/or packaging of the individualized compound dose of medicines.

The device 1 comprises a transport receptacle 5 that is arranged to receive a dose from the dose buffer 2, and to confine it in the receptacle during transport. The transport receptacle 5 is arranged to transport the dose from its dose checking position 3 at the assessment area to a discharge position 12 at a discharge area. The transport receptacle 5 is arranged to receive collected doses of medicines while at the dose checking position 3, via a drop bottom 13 in the dose buffer 2. The transport receptacle 5 is ring shaped, and is arranged to slide over a glass plate 14. The glass plate 14 is hard so that the pills can slide well over its surface. The receptacle 5 is fully open at the bottom and at the top. The open top allows the pills to enter the receptacle and allows inspection of the complete area enclosed by the ring. The open bottom in combination with the glass plate allows the pills in the receptacle to be inspected by the camera from the bottom, and also allows backlight to pass. The inner sides of the wall of the ring include the lights 7 to provide flood lighting of the pills.

At the discharge area 15, the device 1 further includes a discharge that, if the outcome of the check is positive, discharges the received individualized compound dose of medicines to be packaged in a dose compartment of a multi dose compartment package, and if the outcome of the check is negative, discharges the received individualized compound dose of medicines other than to be packaged in a dose compartment of the multi dose compartment package. The discharge area includes a chute 16 connected to an aperture 17 in the hard plate that forms the entry of the chute. The transport receptacle is indexable between the dose checking position 3 and the discharging position 15, as is shown by a double arrow in FIG. 2.

The device 1 further includes a packaging facility, which in this example is integrated in the machine and includes a table 18 arranged to carry a multi dose compartment package, which is embodied as a blister 19. The blister is shown in detail in FIGS. 3a and 3b, and includes an array of dose compartments 20, as well as a blister identification tab 21 with a unique blister code. The blister 19 may be scored, transversely and/or longitudinally, such that individual dose compartments 20 or groups of dose compartments, e.g. rows or columns, may be torn off the sealed blister 19 by a patient, yet remain sealed and provided with unique identification, so that the dose compartments representing upcoming intake moments can be taken along more easily. It should be noted that such a multi dose compartment package is an invention in itself, and may also be used in any other suitable type of prior art device for assessment and/or packaging.

Figure 5:
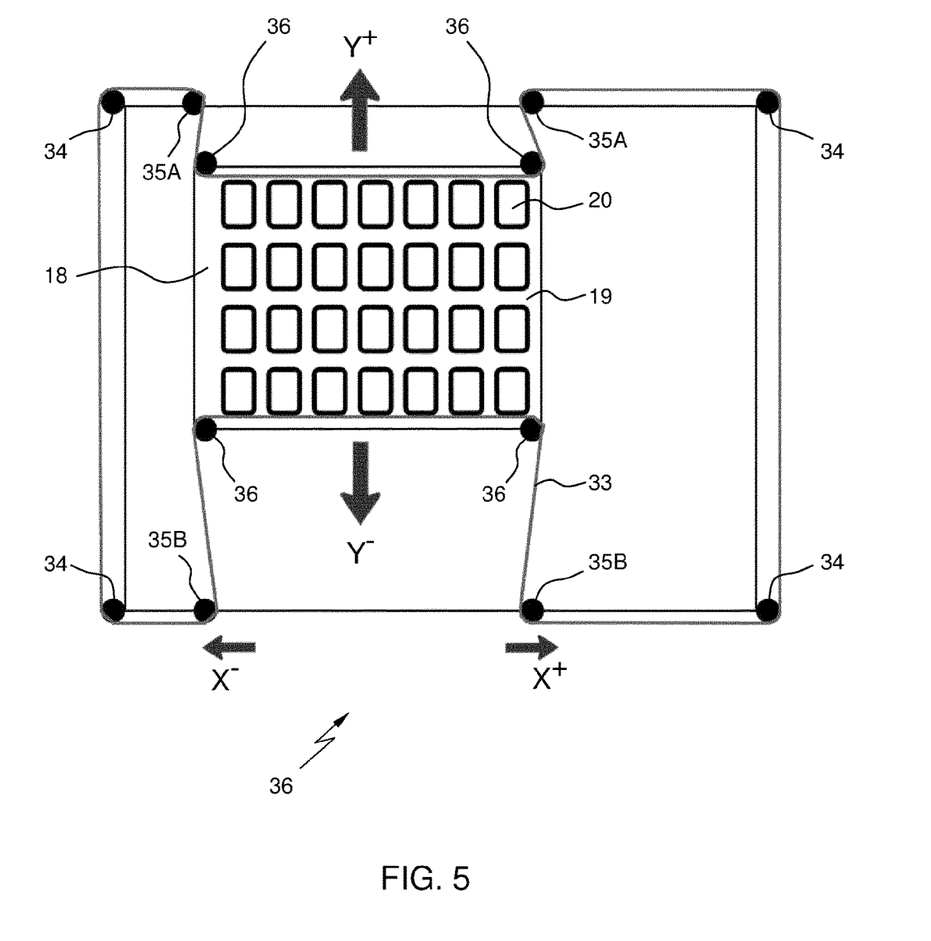
FIG. 5 a schematic top view of an XY positioning table.

As can be seen best in FIG. 1, the table 18 is XY positionable in its plane to align dose compartments 20 of the multi dose compartment blister 19 with a dispensing zone corresponding of the discharge area 15. Here, the dispensing zone corresponds with the exit aperture 22 of the chute 16. An example of a belt drive for the XY positioning of a table carrying a multi dose compartment blister 19 is shown in FIG. 5. A belt 33 is looped around four corner spindles 34 at fixed rectangular corner positions on the frame, two sets of intermediate spindles 35A, 35B that are linearly slidably mounted in the X direction, and around four corner spindles 36 at fixed rectangular corner positions on the table 18. By driving the slidably mounted spindles 35A to move away from each other, and allowing the spindles 35B to move towards each other, the table can move in the Y+ direction, i.e. upward in the drawing. Movement in the Y− direction can be driving the spindles 35A towards each other while the spindles 35B move away from each other. By driving the slidably mounted spindles 35A to slide in the X+ or X− direction, and by allowing the spindles 35B to follow, the table can move to the right or left in the drawing. It shall be clear that such a belt driven XY table positioning device 36 may also be used advantageously in any type of device, in particular for dispensing and/or checking of compound doses of medicines.

Further, the above mentioned XY positioning of a table may also carry a tray such as a intermediate tray, e.g. a buffer tray which may comprise multiple compartments. The buffer tray may be arranged to fill the multi dose compartment blister 19. The buffer tray may first be filled from e.g. the machine 1 with medicines so that it can then fill the multi dose compartment blister 19 at one time. In particular, the buffer tray and the blister 19 may be aligned relative to each other such that the medicines from the buffer tray may be dropped at one time into the compartments of the blister. This way, the blister 19 may continuously be moved in the conveying direction, below the buffer tray and then when the blister and the buffer tray are aligned relative to each other, the blister may be filled with medicines. Beneficially, much more blisters may be filled with medicines within a shorter period. Furthermore, the blister may be indexable, e.g. between a forming apparatus which forms the blister and the buffer tray which then fills the blisters. By correctly timing this process, it may be achieved that there are no hold up of blisters in the conveying direction and the filling of the blisters may be a continuous process.

Alternatively, it is also possible that the buffer tray comprises at least one row and/or column, in particular one row or one column. The buffer tray may then only be moved in the same direction as the conveying direction of the blister or be moved transverse to it. This way, only a row and or column of the buffer tray may be filled with medicines such that a row and/or column of the multi dose compartment blister may be filled with medicines by the buffer tray at one time.

The device 1 further includes a disposal bin 23 for holding incorrect doses. The disposal bin 23 is aligned with the exit aperture 22 to receive doses when the table 18 is positioned away from the discharge area 15, and leaves the path between the exit aperture 22 and the bin free 23.

The device 1 further includes a reader unit 24 for reading the blister code on a blister identification tab 21. The device 1 further includes a writer unit (not shown) to write codes on individual dose compartments 20 of the blister 19.

Figure 4:
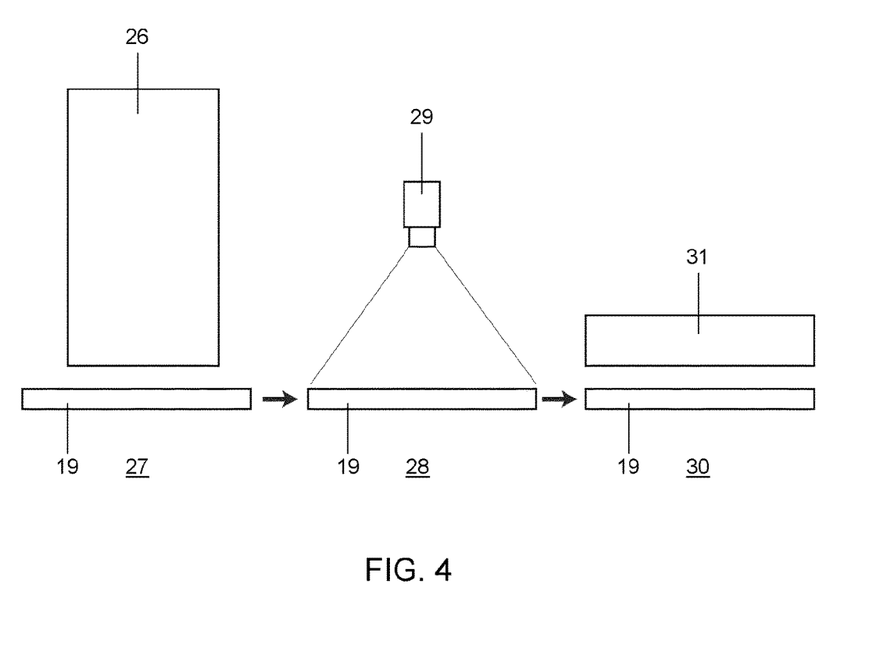
FIG. 4 a schematic side view of three final packaging steps for a multi dose compartment blister package.

Referring to FIG. 4, a schematic side view of three final packaging steps for a multi dose compartment blister package are shown. A first step is shown, with a blister 26 having a blister package 19 at a blister fill position 27. A next step is shown, with the fully filled blister package 19 at a blister photo position 28, and a full blister camera 29 to take a picture of the fully filled blister package 19. A final step is shown, with the blister package 19 at a blister seal position 30, and a blister sealing station 31 sealing the blister package 19.

The machine 1 may be provided with a separate packaging facility, or with an integrated packaging facility, or both. The packaging facility may be arranged to package the individualized compound doses of medicines in a blister type of package as discussed above, or in an other type of packaging, e.g. strips of individual bags. The packaging may be ready made, but may also be formed at the packaging facility, e.g. from a strip of plastics material that is folded double and along its length provided with spaced transverse seals to form into individual compartments that are each filled with a dose of medicines, closed and sealed.

Figure 6:
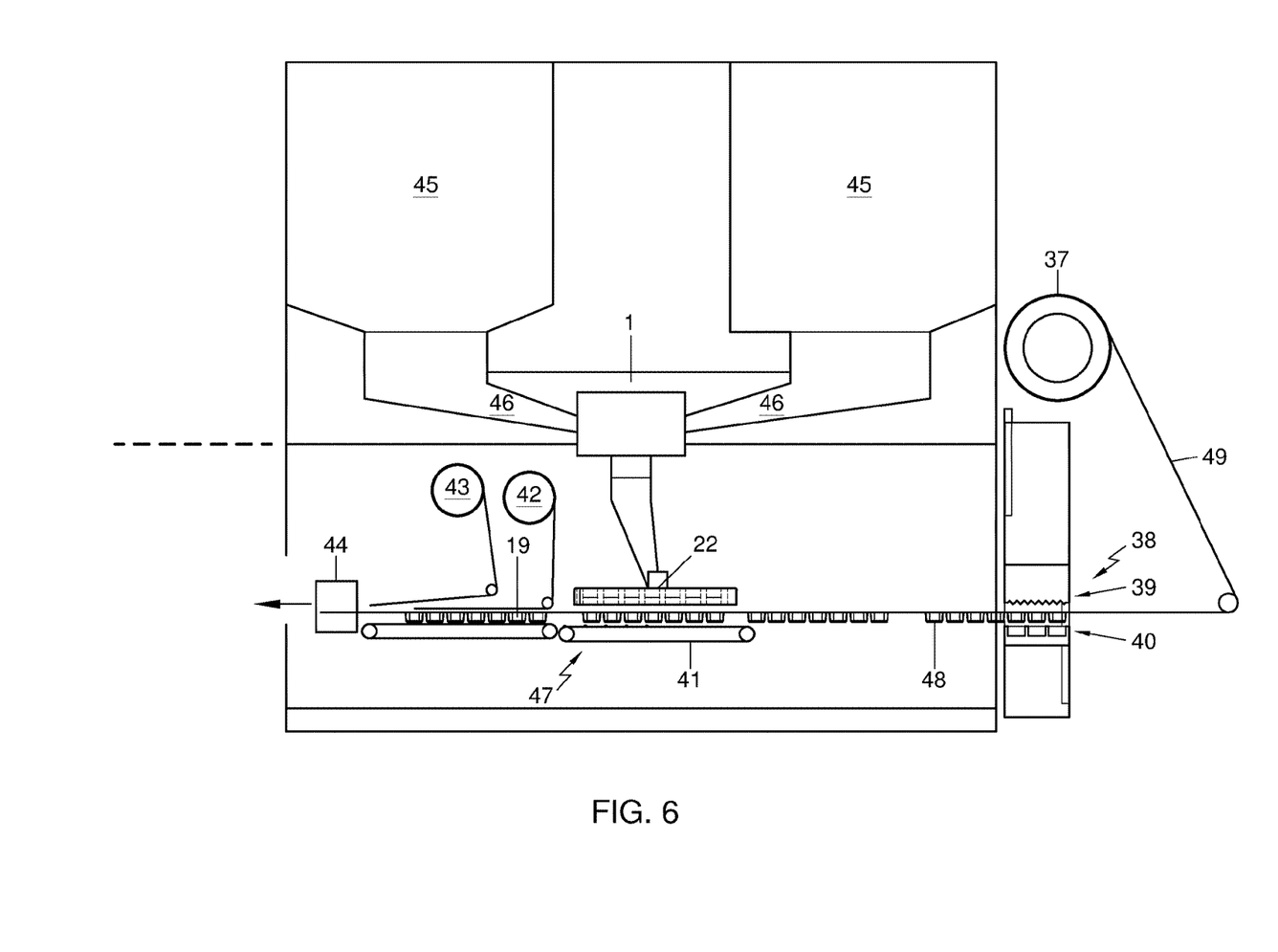
FIG. 6 a schematic side view of a device for receiving and checking individualized compound doses of medicines with integrated packaging facility.

Referring to FIG. 6, another type of packaging facility 47 is shown that is integrated with the machine 1, and that forms multi dose compartments as blister packages 19. The packaging facility 47 forms trays 48 from a continuous web 49 of film that is supplied form a supply roll 37. The trays 48 are formed on a the 40 using a forming apparatus 38, in particular a vacuum forming, thermoforming or vacuum-assisted thermoforming apparatus. When thermoforming, the web of film 49 passing through the forming apparatus 38 is heated using a heater 39 opposite the die 40. By using the die 40 repeatedly for forming one tray 48, the number of compartments in each tray may be varied. The width and length of the trays 48 that are formed may thus vary. The trays 48 are subsequently fed along the dispensing zone 22 using a conveyor 41, so that compartments 20 may be filled. In FIG. 6 it is shown that the medicines are dispensed in dispensers 45 from individual stores of medicines, and travel via chutes 46 to the receiving area 2 of the apparatus 1. In this embodiment, the dispensing zone 22 is arranged to be placed selectively above the subsequent dose compartments 20 that are to be filled with the individualized, compound doses of medicines that have been checked.

The conveyor 41 drives the advancement of the web of film 49. After filling, the trays 48 are sealed with sealing film 42 from a supply roll, labelled with labels from a supply roll of labelling material 43. The advancement of the web of film 49 drives the dispatching of sealing film 42 and labelling material 43. Finally, the filled, sealed and labelled trays 48 in the web of film 49 are cut with a cutter 44 to form individual blister packages 19.

Method of Operation

The medicines in the individualized, compound doses are typically pills, which may include tablets, capsules, caplets, gelcaps, liquigels and softgels. These medicines are dispensed in an automated dispenser (not shown) from selected ones of a plurality of storages of mutually different medicines in accordance with a record for an individualized compound dose of medicines. Such storages include a plurality of pill cassettes, each holding a plurality of pills. The pill cassettes include vanes that can be actuated to release one pill at a time into a chute towards a receiving area. A typical dispenser machine is disclosed at www-.tosho.cc with type number Xana-4001U2. The medicines may also be dispensed at least partially manually, e.g. in multi dose compartment trays with drop bottoms. The doses may also include liquids, e.g. in vials, may e.g. be added to the receiving area and/or dose compartment manually. It should be noted that a series of individualized doses may also include doses which include only a single medicine. For example, custom made or specialty medicines may be manually entered into the dose compartments of a multi dose compartment tray with drop bottoms. The machine 1 may be provided with a plurality of such 'manual' trays, which may be prepared separately and may e.g. be provided with an ID, for example an RFID tag. The ID of this 'manual tray' may then be read by the machine 1, so as to identify the medicines that are intended to be in each of the compartments. The compartments may each in turn be emptied via their drop bottom so that the medicines contained therein may be released via the chute to the receiving area, so that the medicines can be checked. If desired, manually entered medicines may then be combined with automatically dispensed medicines in an individualized compound dose of medicines.

In practice, for each of a series of subsequent intake moments, pills are dispensed in accordance with a patient prescription record and are dropped in the dose buffer 2 of the machine 1. In the dose buffer 2, the pills are collected to form an individualized compound dose of medicine. After collection, the composition of each dose is individually assessed and checked against the patient prescription record for that dose.

When the dose is collected in the buffer 2, the drop bottom 13 opens and forms a chute that conveys the dose to the transport receptacle 5, which is at the dose checking position 3. The receptacle 5 receives the dose via its open top, and holds the pills, which lie on the glass plate 14. The drop bottom 13 closes again, and the dose buffer 2 starts to collect a new dose.

Meanwhile, the shaker 8 engages the receptacle 5 to ensure all pills lie free of each other on the glass plate, and clear from the wall of the receptacle 5.

The top camera 6 and the bottom camera each take a color picture of the pills in the dose. In addition, the top camera 6 takes a contrast picture against light passing through the glass bottom into the receptacle 5.

The composition of individualized compound doses of medicines contained in the receptacle 5 is assessed via automated recognition. The assessment includes analyzing the picture to extract pill identifying characteristics, including e.g. size, shape, color, texture and markings. The photo is compared to images stored in a database or library. This process is known per se, and is e.g. disclosed in WO02/25568 and WO 2005/017814. If the pills are not clear of each other or of the wall of the receptacle 5, the shaker 8 is reactivated. Also, the head 10 of the spectroscopy device 9 may be positioned by the arm 11 at the center of the pill, using information of the photo, e.g. to eliminate doubts in case the visual information collected is not yet enough to identify a specific pill, or e.g. to verify that a pill is genuine and not a fake.

After checking in the assessment area, the receptacle 5 is slid along the glass plate 14 to the discharge position 12. Here, the pills exit 'the receptacle 5, and fall via the aperture 17 into the chute 16. After discharge, the receptacle 5 is returned to the dose check position 3. In this example, checking takes place before discharging to be packaged and packaging of the individualized compound dose of medicines.

When a dose check is positive, the multi dose compartment blister package 19 of the packaging facility is indexed and positioned with a dose compartment 20 thereof to receive a discharged individualized compound dose of medicines. The blister package 19 is moved by the table 18 to have the position of a selected dose compartment 20 to correspond with the exit aperture 22 of the chute 16 connected to the discharging area before the transport receptacle 5 arrives at the discharge position 12.

When a dose check is negative, the multi dose compartment blister package 19 is virtually indexed to a next compartment 2, but the table 18 moves the blister package 19 away so that it leaves the path from the exit aperture 22 to the disposal bin 23 free, and the dose is disposed in the bin 23.

After discharge of a received and checked individualized compound dose of medicines, the discharging area 15 is inspected for any remaining medicines using a drop clearance camera 25. A digital photo, of the discharging area 15 after discharge is stored in a record for the individualized compound dose of medicines, along with a photo of the dose in the receptacle 5 taken at the assessment area 3.

For each received individualized compound dose of medicines, the blister package 19 is virtually indexed to another free dose compartment 20. If the outcome of the check is negative, however, that dose compartment is skipped, and remains open to receive an individualized compound dose of medicines. If the outcome of a check is negative, a plurality of medicines to form an individualized compound dose of medicines according to that record is be received a second time in a subsequent collection step, and the multi dose compartment package is indexed to the skipped dose compartment to package the individualized compound dose of medicines. This indexation again take place in case the check on the composition of the dose that is received a second time, is positive.

The packaging process may continue with packaging a of buffered dose that is found to have a correct composition in a compartment assigned thereto, and a gap in a string of compartments packaged with doses may thus be temporarily formed at the compartment that corresponds to the incorrectly composed dose. This gap can be filled later when a correctly composed dose for that package is discharged to be packaged.

Figure 3A:
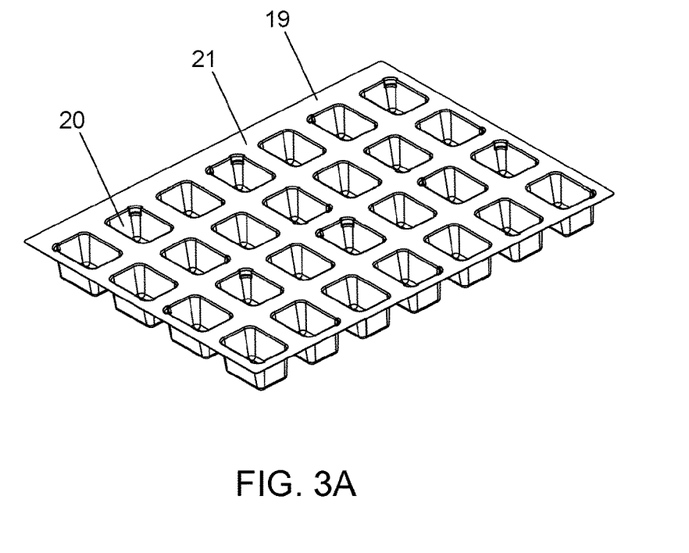
FIG. 3a and FIG. 3b respectively a schematic perspective view and a schematic top view of a multi dose compartment blister package.
Figure 3B:
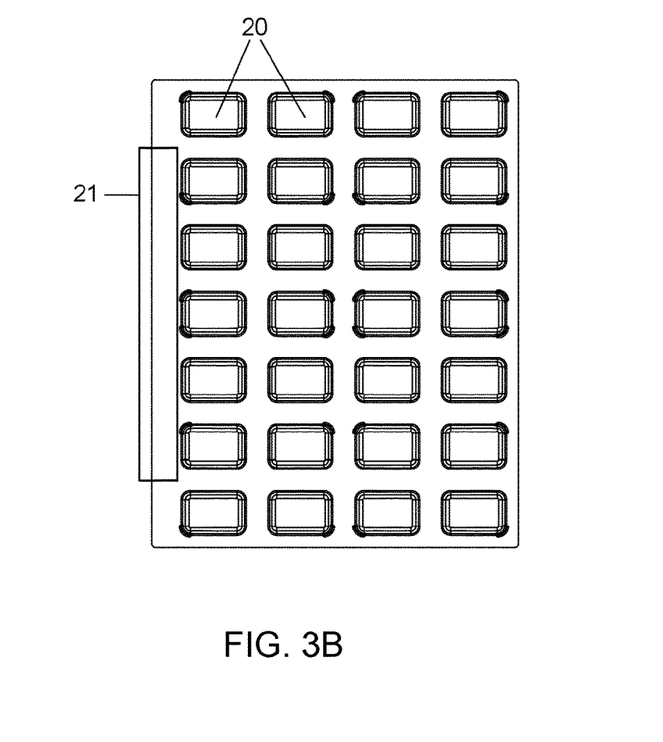

The dose compartments 20 in the multi dose compartment blister package 19 are each dedicated for the individualized compound doses of medicines according to their specific record. Upon discharge of the dose, the dose compartments are each provided with a number and/or text printed thereon by the printing unit. The number and/or text forms a unique physical identifier for the individualized compound dose of medicines in or for that compartment.

Before receiving the first dose, the multi dose compartment blister package 19 carried on the table 18 is read using the reader unit 24, to verify it has the correct configuration for the medicine records to be received.

Referring to FIG. 4, when all compartments 20 of the blister package 19 are filled in accordance with the records, the blister package 19 is transported by blister 26 to the blister fill position 27. Here, also items may be added manually which are not easy to be collected automatically, e.g. sticky pills and/or vials and syringes. Next, a picture is taken of the full blister at the blister photo position 28, using full blister camera 29. The photo is stored with the other pictures in the records. Subsequently, the blister package 19 moves to the blister seal position 30, where it is sealed by the blister seal station 31.

The invention is not limited to the exemplary embodiment represented here. For example, the device may include a plurality of receptacles, e.g. arranged on a rotating carousel. Further, the device may include a different packaging device, e.g. device carrying separate dose compartments, or e.g. a sealable film device. Also, the machine may include one, two or more auxiliary input means via which medicines can be fed to the receiving area or checking area. Such auxiliary input means may be auxiliary to a main input means formed by an automated dispenser machine that includes a plurality of medicine storage cassettes. One or more auxiliary input means may be embodied as trays with a plurality separate compartments for manual placement of medicines therein, and transfer means, such as e.g. a drop bottom associated with a chute to transfer the medicines to the receiving or checking area. In such auxiliary input means, individual or groups of medicines may be placed in each compartment, and the medicines may thus at the reception area or the checking area be added to individual or groups of medicines received from an automated dispensing machine, to form an individualized dose of medicines that is to be checked. As an alternative, the auxiliary input means may be used to manually compound the individualized doses of compound medicines. The manual input via the auxiliary input means may be operated in accordance with a list indicating which medicines are to be placed manually in selected ones of the compartments in accordance with subsequent records for individualized compound doses of medicines.

Such variations shall be clear to the skilled person and are considered to fall within the scope of the invention as defined in the following claims.

LIST OF REFERENCE SIGNS

1. Device
2. Receiving area/Dose buffer

3. Assessment area/Dose check position
4. Automated recognition apparatus
5. Receptacle
6. Top camera
7. Lights
8. Shaker
9. Spectroscopy device
10. Spectroscopy head
11. Positioning arm
12. Discharge position
13. Drop bottom
14. Glass plate
15. Discharge area
16. Chute
17. Aperture chute
18. Table
19. Multi dose compartment blister package
20. Dose compartment
21. Blister identification tab
22. Dispensing zone/Exit aperture
23. Disposal bin
24. Reader unit
25. Drop clearance camera
26. Blister
27. Blister fill position
28. Blister photo position
29. Full blister camera
30. Blister seal position
31. Sealing station
33. Belt
34. Corner spindles frame
35A. Set of slidably mounted spindles
35B. Set of slidably mounted spindles
36. Corner spindles table
37. Roll of tray material
38. Thermoforming apparatus
39. Heater
40. Die
41. Conveyor
42. Roll of sealing material
43. Roll of labelling material
44. Cutter
45, Dispenser
46. Chute
47. Packaging facility
48. Trays
49. Web of film

The invention claimed is:

1. A method of receiving and checking individualized compound of medicines, comprising the steps of
   receiving a plurality of dispensed medicines that form an individualized compound dose of medicines,
   assessing the composition of the individualized compound dose of medicines through automated recognition of the received medicines,
   checking the assessed composition of the received individualized compound dose of medicines against a record for the composition of that individualized compound dose of medicines, and
   indexing a multi dose compartment package virtually and/or physically to a free dose compartment,
   if the outcome of the check is positive, discharging the received individualized compound dose of medicines to be packaged into the free dose compartment of the multi dose compartment package, and
   if the outcome of the check is negative, skipping the indexed free dose compartment so that it remains open to receive an individualized compound dose of medicines and indexing the multi dose compartment package virtually and/or physically to a next free dose compartment.

2. The method of claim 1, wherein a previously received individualized compound dose of medicines is being assessed and/or checked while a following individualized compound dose of medicines is being received.

3. The method of claim 1, wherein after reception in a reception area, a received individualized compound dose of medicines is moved to a separate assessment area for checking.

4. The method of claim 1, wherein a received and checked individualized compound dose of medicines is discharged, while a subsequently received individualized compound dose of medicines is being assessed and/or checked.

5. The method of claim 1, wherein after checking in a checking area, a received and checked individualized compound dose of medicines is moved to a separate discharging area for discharging.

6. The method of claim 1, wherein after discharge of a received and checked individualized compound dose of medicines, a discharging area is inspected for any remaining medicines.

7. The method of claim 1, wherein if the outcome of a check is negative, a plurality of medicines to form an individualized compound dose of medicines according to the record for the composition of that individualized compound dose of medicines is received a second time, and the multi dose compartment package is indexed to the skipped dose compartment to package the individualized compound dose of medicines.

8. The method of claim 1, wherein the dose compartment in the multi dose compartment package is dedicated for the individualized compound dose of medicines according to the record for the composition of that individualized compound dose of medicines.

9. The method of claim 1, wherein the compartment is provided with an unique identifier for the individualized compound dose of medicines in or for that compartment.

10. The method of claim 1, wherein the dose compartments in the multi dose compartment package are closed only after the individualized compound doses of medicines for that package have been packaged.

11. The method of claim 1, wherein the composition of individualized compound doses of medicines contained in dose compartments of the package is assessed via automated recognition of the medicines contained in compartments, and is checked against a record for the composition of the individualized compound dose of medicines for that compartment.

12. The method of claim 1, further comprising a first step of automatically dispensing medicines from selected ones of a plurality of storages of mutually different medicines in accordance with a record for an individualized compound dose of medicines.

13. The method of claim 1, further comprising a first step of manually dispensing mutually different medicines in accordance with a record for an individualized compound dose of medicines.

14. A device arranged to receive and check individualized compound doses of medicines in accordance with claim 1.

15. A device for receiving and checking individualized compound doses of medicines, comprising
   a receiving area for receiving a plurality of dispensed medicines that form an individualized compound dose of medicines, an assessment area with automated recognition apparatus for assessing the composition of the individualized compound dose of medicines through automated recognition of the received medicines, a computer that checks the assessed composition of the received individualized compound dose of medicines against a record for the composition of that individualized compound dose of medicines and indexes the multi dose compartment package virtually and/or physically to a free dose compartment;

a discharge that, if the outcome of the check is positive, discharges the received dose of the individualized compound dose of medicines to be packaged in the free dose compartment of the multi dose compartment package, and if the outcome of the check is negative, skips the indexed free dose compartment so that the free dose compartment remains open to receive an individualized compound dose of medicines and indexes the multi dose compartment package virtually and/or physically to a next free dose compartment.

16. The device according to claim 15, wherein the receiving area is embodied as a dose buffer that is physically separate from the checking area.

17. The device according to claim 16, further comprising a number of transport receptacles that are arranged to receive a dose from the dose buffer, and to confine it in the receptacle during transport.

18. The device according to claim 17, wherein the transport receptacles are arranged to transport the dose from an assessment area to a discharge area.

19. The device according to claim 18, wherein the transport receptacles are arranged to be indexable.

20. The device according to claim 19, wherein the receptacles are slidably disposed on a hard bottom plate.

21. The device according to claim 20, wherein the discharge area includes a chute connected to an aperture in the bottom plate.

22. The device according to claim 15, comprising a table for carrying a multi dose compartment package, which is table is positionable in its plane to align an indexed free dose compartments of the multi dose compartment package with the dispensing zone.

23. The device according to claim 22, further including a reader unit for reading a code on a multi dose compartment package carried on the table.

24. The device according to claim 15, further including auxiliary input means to manually compound the individualized doses of compound medicines.

25. A system for checking individualized compound doses of medicines, comprising:
at least one first processor; and
a first non-transitory computer readable medium communicatively coupled to the at least one first processor, the first non-transitory computer readable medium having stored thereon computer software comprising a first set of instructions that, when executed by the at least one first processor, causes the system to:
assess a plurality of dispensed medicines that form an individualized compound dose of medicines,
determine a composition of the individualized compound dose of medicines through automated recognition of the received medicines,
check the assessed composition of the received individualized compound dose of medicines against a record for the composition of that individualized compound dose of medicines,
index a multi dose compartment package virtually and/or physically to a free dose compartment,
if the outcome of the check is positive, discharge the received dose of the individualized compound dose of medicines to be packaged into the free dose compartment of a multi dose compartment package, and
if the outcome of the check is negative, skip the free dose compartment so that it remains open to receive an individualized compound dose of medicines and index the multi dose compartment package virtually and/or physically to a next free dose compartment.

* * * * *